(12) United States Patent
Alsalman et al.

(10) Patent No.: US 11,604,179 B2
(45) Date of Patent: Mar. 14, 2023

(54) GAS SENSOR TESTING SYSTEM AND METHOD

(71) Applicant: Saudi Arabian Oil Company, Dhahran (SA)

(72) Inventors: Ala'A Alsalman, Sayhat (SA); Adam Alawwami, Dhahran (SA); Abdulaziz Hudaifah, Dhahran (SA); Faisal Al-Oufi, Damman (SA); Reem Alnoaimi, Dhahran (SA); Saad Almughairah, Dammam (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 328 days.

(21) Appl. No.: 16/799,589

(22) Filed: Feb. 24, 2020

(65) Prior Publication Data
US 2021/0262997 A1    Aug. 26, 2021

(51) Int. Cl.
*G01N 33/00* (2006.01)
(52) U.S. Cl.
CPC ... *G01N 33/007* (2013.01); *G01N 2033/0072* (2013.01)
(58) Field of Classification Search
CPC ......... G01N 33/007; G01N 2033/0072; G01N 2035/0403; G01N 2035/0405
See application file for complete search history.

(56) References Cited

U.S. PATENT DOCUMENTS

| | | | |
|---|---|---|---|
| 3,204,859 A | 9/1965 | Crooks | |
| 3,744,537 A * | 7/1973 | Cole | B67D 1/0468 |
| | | | 141/4 |
| 4,322,964 A | 4/1982 | Melgaard et al. | |
| 4,538,447 A | 9/1985 | Pravda | |
| 6,851,316 B2 | 2/2005 | Micke et al. | |

(Continued)

FOREIGN PATENT DOCUMENTS

| CN | 204649366 U | * | 9/2015 |
|---|---|---|---|
| CN | 208109154 U | | 11/2018 |

(Continued)

OTHER PUBLICATIONS

International Search Report and the Written Opinion of the International Searching Authority issued in the prosecution of international application No. PCT/US2021/018615, dated Jul. 21, 2021, 18 pages.

*Primary Examiner* — John Fitzgerald
*Assistant Examiner* — Truong D Phan
(74) *Attorney, Agent, or Firm* — Bracewell LLP; Constance G. Rhebergen; Keith R. Derrington

(57) ABSTRACT

A system and method for testing a gas sensor with a test gas and that recovers the test gas after testing. The test gas is stored in a test gas source, and delivered to the gas sensor through a supply circuit. After the test is completed, gas is withdrawn from the supply circuit into a recycle circuit. A compressor in the recycle circuit pulls the test gas into the recycle circuit, pressurizes the test gas and discharges the pressurized test gas back into the test gas source. Valves are in the supply and recycle circuits, which when selectively opened and closed changes between testing and recycle configurations. The recycle flow is filtered to prevent air and other non-test gas substances from being introduced into the test gas source.

16 Claims, 4 Drawing Sheets

(56) References Cited

U.S. PATENT DOCUMENTS

| | | |
|---|---|---|
| 7,937,984 B2 | 5/2011 | Tobias |
| 9,719,915 B2 * | 8/2017 | Kshirsagar ............. G01N 29/42 |
| 10,338,044 B2 | 7/2019 | Schwieters et al. |
| 2004/0182133 A1 * | 9/2004 | Staphanos .......... G01N 27/4077 73/23.31 |
| 2004/0221919 A1 | 11/2004 | MacNeal et al. |
| 2008/0156071 A1 | 7/2008 | Tobias |
| 2016/0168933 A1 * | 6/2016 | Aktas ...................... E21B 21/01 73/152.43 |
| 2016/0320362 A1 * | 11/2016 | Schwieters ........ G01N 33/0013 |
| 2020/0355659 A1 * | 11/2020 | McEwen .............. G01N 33/007 |

FOREIGN PATENT DOCUMENTS

| | | | |
|---|---|---|---|
| CN | 208223816 U | * 12/2018 | |
| WO | WO-2016203273 A1 | * 12/2016 | ......... F16K 37/0075 |
| WO | 2019152047 A1 | 8/2019 | |

* cited by examiner

GAS SENSOR TESTING SYSTEM AND METHOD

BACKGROUND

1. Field

The present disclosure relates to a system and method for testing a gas sensor that recaptures gas used during testing for reuse later.

2. Description of Prior Art

Gas sensors are sometimes employed to detect an accumulation or presence of certain gases that may have escaped or leaked from a confined space; such as from piping, a valve, a vessel, a reactor, or a furnace. Places where gas sensors are installed include dwellings, manufacturing facilities, refineries, factories, well sites, and vehicles. The gases in question are typically hazardous due to their toxicity, flammability, or both. In these situations a gas sensor is part of a safety system that emits an alarm to alert operations personnel when a hazardous gas is detected. In some instances the safety system is programmed to generate and send commands to shut down processes operating within or near where a hazardous gas is sensed. Most gas sensors are set to initiate an alert signal when a hazardous gas being sensed reaches a threshold concentration in the area around the gas sensor.

Gas sensors are periodically tested or calibrated or both by exposing the sensors to a test or span gas that has a known concentration of a gas the sensor is intended to monitor. The test gas is generally stored in a pressurized test bottle fitted with a valve assembly for releasing the test gas. A length of tubing is generally attached to the valve assembly, which normally has an adapter mounted on its free end. Test gas is typically delivered to the sensor by engaging the adapter with an inlet to the sensor, and then opening a valve on the valve assembly; the test gas then flows through the tubing and to the inlet. A drawback with this approach is that test gas within the length of tubing escapes after testing the gas sensor, which increases fugitive emissions into the atmosphere and depletes available test gas with each usage. Depending on the volume within the test bottle and the amount of test gas required for testing each sensor, test bottles are emptied after being used to test only four or five gas sensors.

SUMMARY

An example of a system for testing a gas sensor is disclosed, and which includes a test gas source, a supply circuit in selective communication with test gas from the test gas source; where the supply circuit includes supply tubing, and a test cap on an end of the supply tubing that selectively mounts to a sensor inlet on the gas sensor. The system of this example also includes a recycle circuit having a compressor with a compressor inlet that is in selective communication with the supply circuit. In an alternative, the compressor has a compressor discharge that is in communication with the test gas source. The supply circuit is optionally in communication with the test gas from the test gas source through a connection coupled with the test gas source. In one embodiment, the supply circuit further includes a supply valve that is selectively opened and closed and that is between the test gas source and an intersection between the supply circuit and the recycle circuit. A recycle valve is optionally included in the recycle circuit that is selectively opened and closed and that is between the compressor and an intersection between the supply circuit and the recycle circuit. In one example, the supply circuit is in selective communication with the test gas through a manifold type fitting having multiple openings, and where the fitting is coupled with the test gas source. In this example, the compressor includes a discharge that is in communication with the test gas in the test gas source through the fitting. In one embodiment, the test gas source is a portable bottle, and the compressor is mounted to an exterior of the bottle. Alternatively, a filter is in the supply circuit that contains an air blocking material. In an example, the test cap includes a chamber that receives the sensor inlet, and seals on the inner surface of the chamber that define a pressure barrier between the test gas in the supply circuit and ambient.

Also included is a method of gas sensor testing that includes exposing a gas sensor to an amount of test gas from a test gas source and recapturing the amount of the test gas. The method optionally includes monitoring a response of the gas sensor. In one alternative, the method includes directing the amount of test gas that is recaptured back to the test gas source. One embodiment of the method includes testing another gas sensor by directing another amount of test gas from the test gas source to the another gas sensor, and recapturing the another amount of test gas. In an alternative, the amount test gas is directed to a gas sensor inlet on the gas sensor and through a supply circuit that is in communication with the test gas source, and where the step of recapturing the amount test gas involves drawing the amount of test gas into a recycle circuit. In this example, a compressor is disposed in the recycle circuit and which is activated to draw the amount of test gas into the recycle circuit, and where a discharge of the compressor directs the amount of test gas back to the test gas source. Options exist where the test gas source is a portable bottle, and where the compressor mounts to the bottle. Further in this example, the test gas source, compressor, supply circuit, and recycle circuit make up a gas sensor testing system, the method further includes moving the gas sensor testing system to another gas sensor, exposing the another gas sensor to another amount of test gas, recapturing the another amount of test gas. In one embodiment, the method further includes filtering non-test gas substances that have mixed with the amount of test gas during the step of recapturing the amount of test gas.

BRIEF DESCRIPTION OF DRAWINGS

Some of the features and benefits having been stated, others will become apparent as the description proceeds when taken in conjunction with the accompanying drawings, in which.

Figure 1:
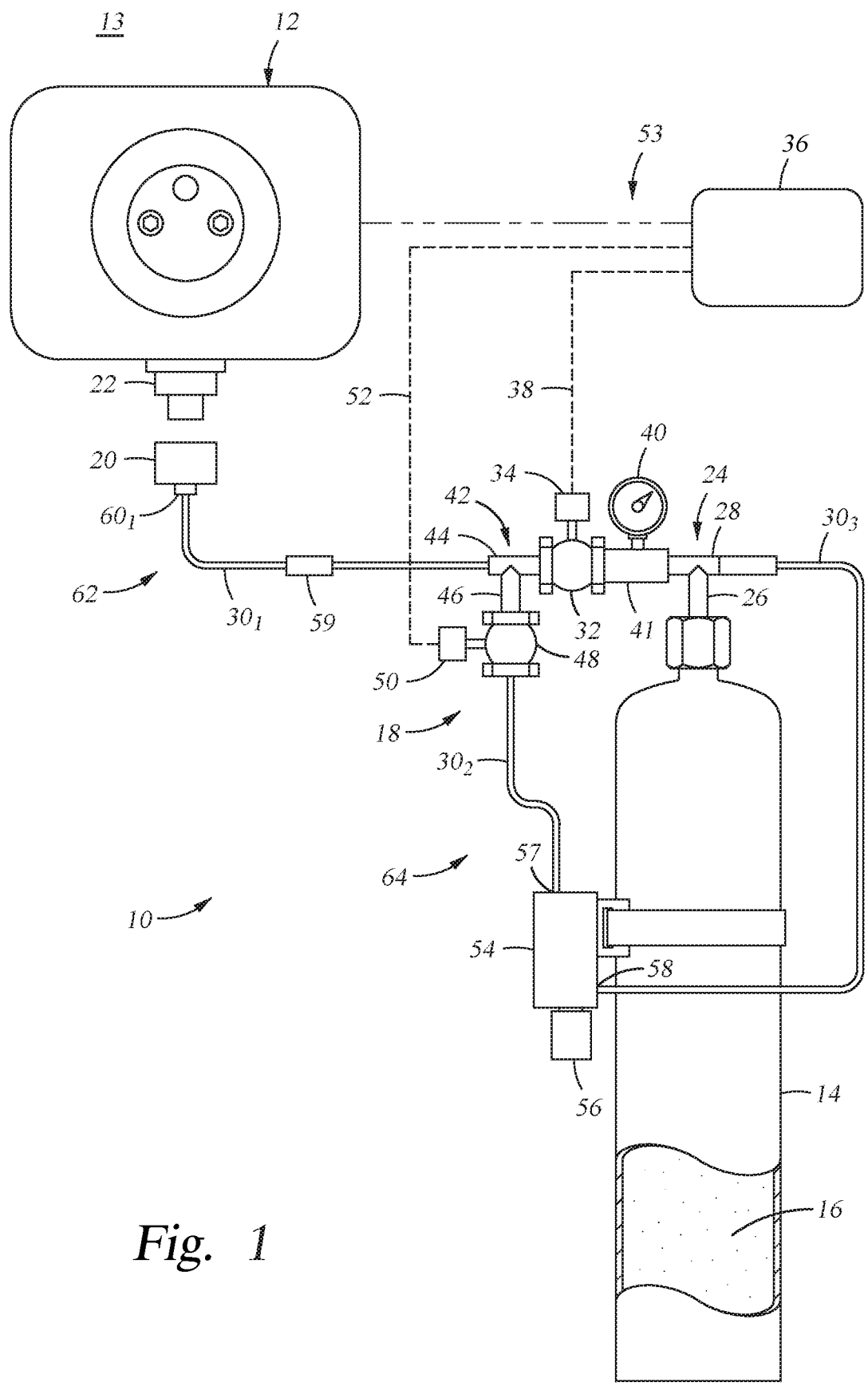
FIG. 1 is a schematic depiction of an example of a gas sensor and of a gas sensor testing system.

While the advancement will be described in connection with the preferred embodiments, it will be understood that it is not intended to limit the advancement to that embodiment. On the contrary, it is intended to cover all alternatives, modifications, and equivalents, as may be included within the spirit and scope of the advancement as defined by the appended claims.

DETAILED DESCRIPTION

The method and system of the present disclosure will now be described more fully hereafter with reference to the accompanying drawings in which embodiments are shown. The method and system of the present disclosure may be in many different forms and should not be construed as limited to the illustrated embodiments set forth here; rather, these embodiments are provided so that this disclosure will be thorough and complete, and will fully convey its scope to those skilled in the art. Like numbers refer to like elements throughout. In an embodiment, usage of the term "about" includes +/−5% of a cited magnitude. In an embodiment, the term "substantially" includes +/−5% of a cited magnitude, comparison, or description. In an embodiment, usage of the term "generally" includes +/−10% of a cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Shown in a perspective view in FIG. 1 is an example of a gas sensor testing system 10 that is used for testing a gas sensor unit 12. In an example, the gas sensor unit 12 is used for detecting and/or monitoring for the presence of a specific substance in a location 13, examples of the substance includes those that are toxic, volatile, flammable, combustible, and combinations. The types of substances include gas, liquid, and particulate matter such as smoke. In an example, toxic substances are those that by themselves pose a health risk, such as but not limited to hydrogen sulfide and carbon dioxide. Also, for the purposes of discussion herein embodiments exist where testing is an evaluation to determine if the gas sensor unit 12 senses a particular gas in any concentration. In another example, testing involves calibrating the gas sensor unit 12 so that when a known concentration of a particular substance is in the location 13 where the gas sensor unit 12 is disposed, steps are taken to adjust the gas sensor unit 12 so that the output from the unit accurately reflects that known concentration.

In the example of FIG. 1, the gas sensor testing system 10 includes a container 14 which is shown having a span gas or calibration gas 16 (referred to herein as a test gas) within the container 14. Examples of the container 14 include portable bottles designed to retain pressurized fluids within. Examples of the test gas 16 include a gas made of substantially the same material, and a combination of different gases but where the concentrations of one or more gases within are known. An example of a test gas circuit 18 is schematically illustrated that is included with gas sensor testing system 10 and is shown having a test cap 20, which is configured to receive a sensor inlet 22 within. The test gas 16 within container 14 is introduced into the test gas circuit 18 via a primary T-connection 24. In the illustrated example, primary T-connection 24 includes a takeoff portion 26 which is an annular member that couples with the container 14 and provides communication of the test gas 16 into an annular inline portion 28. As shown, an end of takeoff portion 26 intersects a mid-portion of inline portion 28; axial bores (not shown) in portions 26, 28 are in communication with one another through an opening in a sidewall of inline portion 28. In the example of FIG. 1, the primary T-connection 24 resembles a manifold-like connection having multiple openings that are in communication with one another. Test gas circuit 18 includes lengths of tubing $30_{1-3}$ and which provide conduits for directing the test gas 16 from the container 14 to test cap 20. As will be described in more detail below, the lengths of tubing $30_{1-3}$ provide a way for recapturing the test gas 16 released from within container 14.

Further in the example of FIG. 1, a supply valve 32 is shown disposed in the test gas circuit 18 and having opposite ends communicating with the tubing $30_1$ and primary T-connection 24. In an embodiment, an actuator 34 is coupled with the supply valve 32; in examples actuator 34 is an electrically powered motor, is pneumatically powered, or is a manually operated hand wheel. In one alternate embodiment, a controller 36 is included and shown in communication with the actuator 34 via a control line 38. Alternate examples of operation exist where signals from controller 36 are delivered to actuator 34 through control line 38 and for actuating supply valve 32 between an opened configuration and a closed configuration. Optionally, partially open/closed configurations are also envisioned in one embodiment of the gas sensor testing system 10. An optional pressure gauge 40 is shown included with the test gas circuit 18, and mounted onto an annular housing 41 whose opposing ends connect to supply valve 32 and to primary T-connection 24. Alternatively tubing is substituted for the body 41, or the valve 32 attaches directly to primary T-connection 24. Further optionally, examples exist with pressure gauge 40 mounts onto primary T-connection 24, or on tubing $30_3$.

The test gas circuit 18 shown includes a diverting T-connection 42 that provides communication between tubing $30_1$ and tubing $30_2$. As shown, diverting T-connection 42 includes an annular inline portion 44 disposed between the tubing $30_1$ and supply valve 32. An annular take-off portion 46 intersects a mid-section of inline portion 44, and bores (not shown) in portions 44, 46 are in communication through an opening in a sidewall of inline portion 44. An end of take-off portion 46 opposite inline portion 44 couples to a recycle valve 48. An actuator 50 couples with the recycle valve 46 that also is in communication with controller 36 via control line 52, and examples exist where the recycle valve 46 operates by opening and closing and/or intermediate positions in response to signals from controller 36 via control line 52. Similar to actuator 34, embodiments of actuator 50 include a device that is electrically powered, pneumatically powered, and manually operated. In one alternative, a communication link 53 is between controller 36 and gas sensor unit 12, and examples of the communication link 53 include hardwire, wireless, and fiber optic.

Still referring to the example of FIG. 1, a compressor 54 is shown mounted onto the outer surface of container 14, and with a power source 56. In an embodiment, power source 56 is in electrical communication with compressor 54 and provides electricity for powering compressor 54. In an example, power source 56 includes a rechargeable lithium battery. As shown, compressor 54 includes an inlet 57 and a discharge 58. Tubing $30_2$ is illustrated having an end connected to a side of recycle valve 48 opposite diverting T-connection 42, another end of tubing $30_2$ connects to the inlet 57 of compressor 54. An end of tubing $30_3$ is shown connected to the discharge 58 of compressor 54. An opposite end of tubing $30_3$ connects to a side of primary T-connection 24 opposite housing 41. An optional filter 59 is provided inline within tubing $30_1$ between test cap 20 and supply valve 32. In another alternative, tubing connections $60_1$, $60_2$ are shown on ends of lengths of tubing $30_1$, $30_3$. Embodiments exist where a tubing connection is provided on each end of the lengths of tubing $30_1$, $30_2$, $30_3$.

Figure 2:
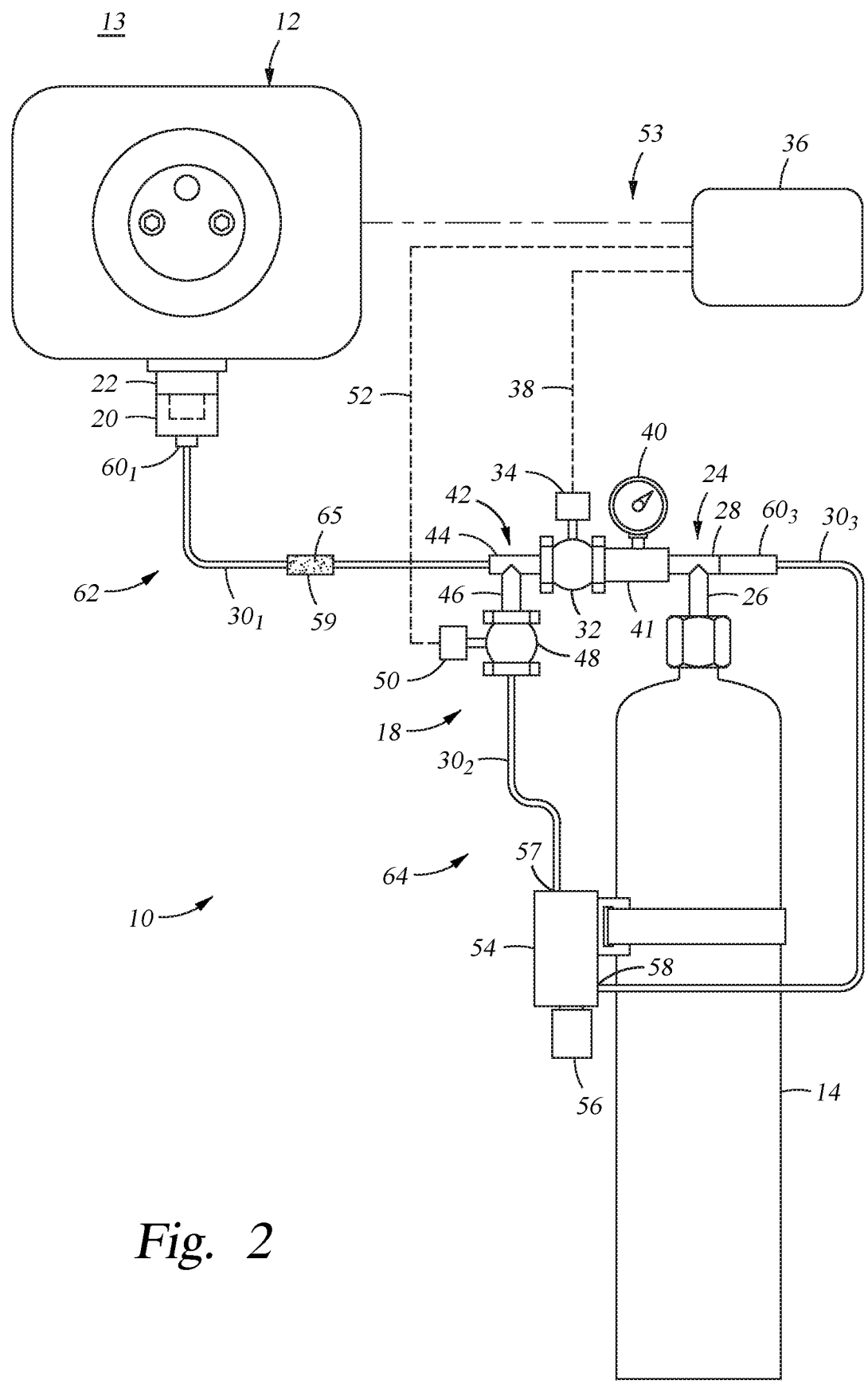
FIG. 2 is a schematic view of an example of the gas sensor of FIG. 1 being tested by the testing system.

Referring now to FIG. 2, a non-limiting example of operation of the gas sensor testing system 10 is schematically depicted. In the example illustrated the test cap 20 fitted over the sensor inlet 22 and supply valve 32 is put into an open position so that test gas 16 (FIG. 1) flows from container 14 through the supply valve 32, tubing $30_1$, and into test cap 20, inside the test cap 20 the test gas 16 is exposed to sensor inlet 22. While the test gas 16 is being exposed to the sensor inlet 22, an actual output or response from the gas sensor unit 12 is monitored and compared with an expected output or response of the gas sensor unit 12 based on a knowledge of the test gas 16 composition. In an example, the output or response of the gas sensor unit 12 is an electrical signal that varies in voltage; in alternatives the voltage value or values correlates to one or more of the presence or concentration of a particular substance or gas. In an alternative, if the actual output or response differs from the expected output or response an additional step is undertaken the gas sensor unit 12 is calibrated. In one example of calibrating the gas sensor unit 12, the gas sensor unit 12 is adjusted so that its actual output or response when subjected to the test gas 16 is the same or substantially the same as an output or response expected by subjecting the gas sensor unit 12 to the particular test gas 16. Additional alternatives include determining that the gas sensor unit 12 is accurately sensing gas and is operating properly, or determining that the gas sensor unit 12 is not accurately sensing gas and not operating properly. In an alternative, the output or response from the gas sensor unit 12 is directed via the communications link 53 to controller 36, or visually monitored by an operations personnel.

After testing the gas sensor unit 12, the supply valve 32 is manipulated into a closed configuration which blocks the communication of test gas 16 from the container 14. Recycle valve 46 is then put into an open configuration which provides communication between compressor 54 and an amount of test gas 16 that is disposed within tubing $30_1$, and inside of the T-fitting 44. For the purposes of description herein, the supply valve 32, associated tubing $30_1$ and test cap 20 are referred to as a supply circuit 62; and the recycle valve 46, tubing $30_2$, tubing $30_3$, and compressor 54 are referred to as being part of a recycle circuit 64. With the recycle valve 46 moved into the open configuration and the supply valve 32 in a closed configuration compressor 54 is actuated. Examples of actuating compressor 54 include directing a signal from controller 36 via a communication means (not shown). In an alternative operations personnel activate compressor 54. Actuating compressor 54 reduces pressure within tubing $30_2$ and recycle valve 46, that in turn draws the test gas 16 inside the supply circuit 62 into the recycle circuit 64. As will be described in more detail below, seals are created between the test cap 20 and cap sensor inlet 22 and in the tubing connector $60_1$, which block the flow of ambient air into the test gas circuit 18. In addition to the seals, an optional filter matrix 65 is provided within filter 59 that is configured to block any air that has inadvertently entered the test gas circuit 18. Inside the compressor 54 the recaptured test gas 16 is pressurized and directed to the discharge 58, where it then enters the tubing $30_3$. Inside the tubing $30_3$, the recaptured test gas 16 is directed from within the supply circuit 62 back to the primary T-connection 24 and into the container 14. In an alternative, a check valve (not shown) is disposed within the tubing $30_3$ to block a backflow of pressurized gas within 14 to compressor 54.

Figure 3:
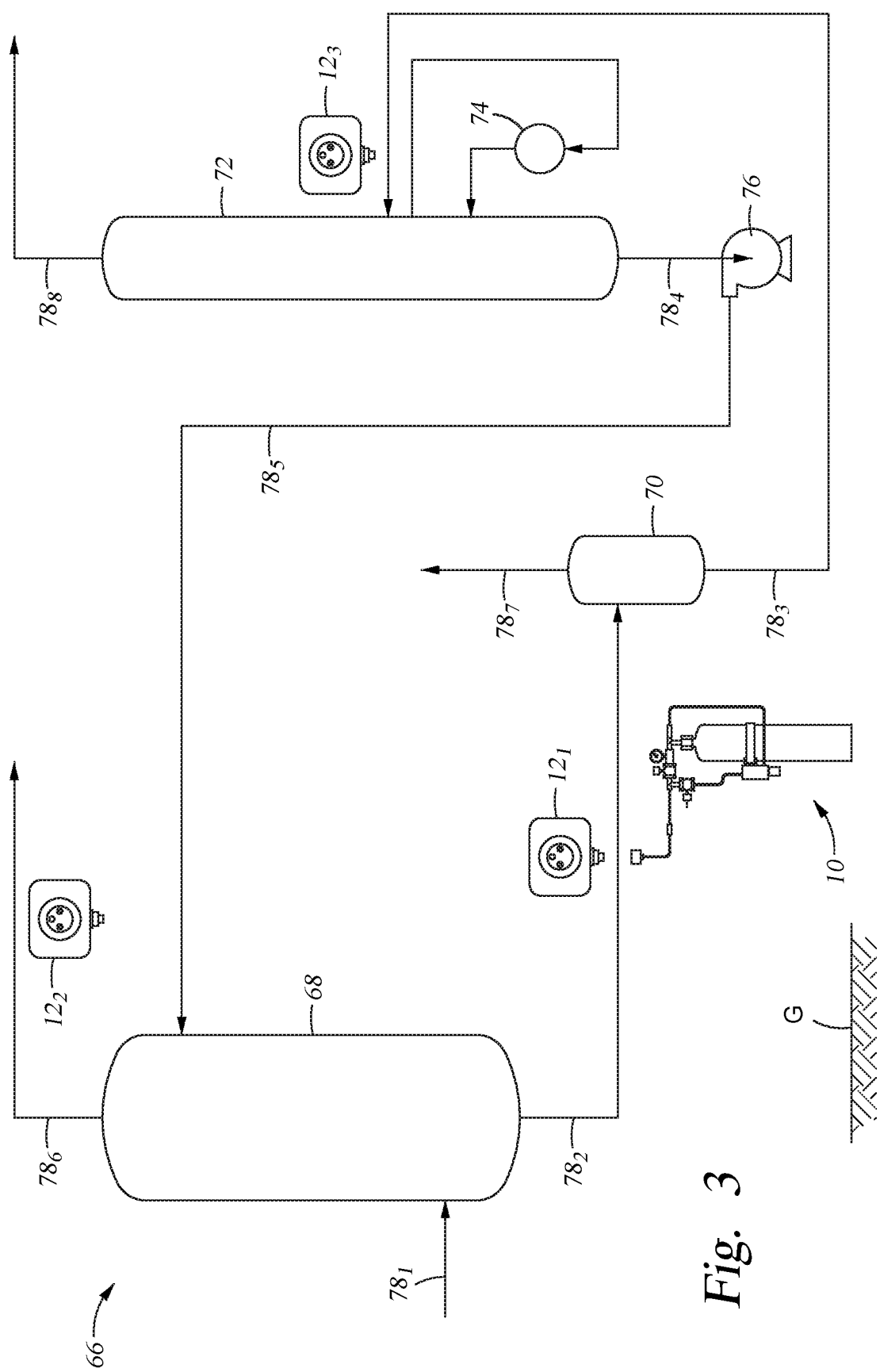
FIG. 3 is a schematic of an example of a processing facility having gas sensors being tested by a testing system.

Significant advantages are realized by recapturing the amount of test gas within the supply circuit 62, such as reducing fugitive emissions, providing a safer work space for operations personnel testing gas sensors, and also preserves the test gas 16 so that multiple gas sensors are tested with test gas from a container that does not require refilling. Referring now to FIG. 3 shown is an example of a processing facility 66 and which includes a number of different gas sensor units $12_{1-3}$ at different locations around the facility 66. Examples of the facility 66 include refineries, chemical processing plants, treatment centers, and any other facility having fluids and there is a desire to monitor if those fluids have escaped from within a closed or sealed environment, such as piping or fluids handling equipment. The example processing facility 66 includes a vessel 68, tank 70, tower 72, heat exchanger 74, pump 76, and lines $78_{1-8}$ that provide a pathway for fluid flow between these different components. In the illustrated example, an embodiment of the gas sensor testing system 10 is depicted adjacent a gas sensor $12_1$ that is disposed along a line $78_2$ carrying bottoms from the vessel 68 to tank 70. Advantages of the portability of the gas sensor testing system 10 is that not only are multiple gas sensor units tested without the need to replace testing gas held within the unit 10, but the portability allows operations personnel to reach sensor units such as sensor unit $12_2$ on an overhead line $78_6$ shown above an upper end of vessel 68. In an alternative, sensor unit $12_3$ is tested and/or calibrated by gas sensor testing system 10. In the example of FIG. 3, gas sensor units $12_{2,3}$ are shown at elevations well above grade G.

Figure 4:
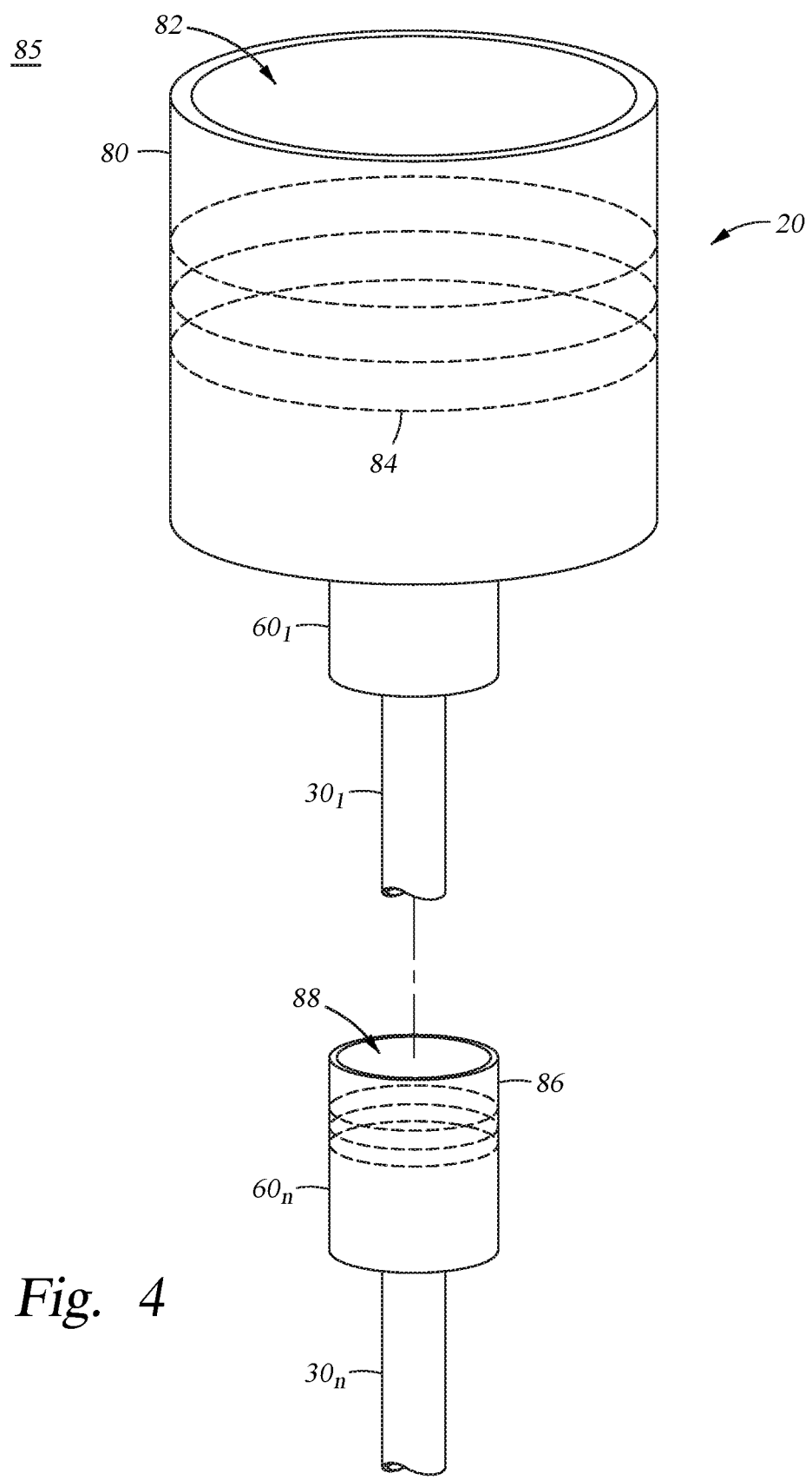
FIG. 4 is a perspective view of an example of a test cap and a tubing connection for use with the testing system of FIG. 1.

Shown in a perspective view in FIG. 4 are examples of the test cap 20 and tubing connection $60_n$. As shown, test cap 20 includes a cylindrical-type housing 80 having a cavity within and which selectively receives the sensor inlet 22 (FIG. 1). To improve sealing between the test cap 20 and sensor inlet 22, a series of O-rings 84 (shown in dashed outline) are provided along an outer surface of cavity 82 and which form a pressure barrier between ambient 84 and into tubing $30_1$. An advantage of the O-rings 84 is that the test gas is retained within the supply circuit 62 (FIG. 2) to block an ingress of air or other substances from ambient 84. Also the example of tubing connector $60_n$ shown includes a cylindrical-type housing 86 with a cavity 88 formed within and also is equipped with O-rings shown in dashed outline on its inner surface which enhanced sealing between where tubing $30_n$ connects to adjacent fluid handling members.

The present advancement described here, therefore, is well adapted to carry out the objects and attain the ends and advantages mentioned, as well as others inherent there. While a presently preferred embodiment of the advancement has been given for purposes of disclosure, numerous changes exist in the details of procedures for accomplishing the desired results. In one alternative, a single multi-ported valve is in place of T-connections 32, 42 and valves 32, 48. These and other similar modifications will readily suggest themselves to those skilled in the art, and are intended to be encompassed within the spirit of the present advancement disclosed here and the scope of the appended claims.

What is claimed is:

1. A system for testing a gas sensor unit comprising:
 a test gas source comprising a portable bottle having a test gas for use in calibrating the gas sensor unit and a T fitting comprising an inline portion with first and second ends, and a takeoff portion having an end connected to the portable bottle and in communication with the test as in the portable bottle and an opposite end intersecting a midsection of the inline portion;

a supply circuit in selective communication with the test gas in the test gas source, the supply circuit comprising,
 a test cap comprising a cylindrical-type housing, a cavity defined within the housing that selectivity received a sensor inlet that is on the gas sensor, and a tubing connection attached to the housing and that is in communication with the cavity, and
 supply tubing having an upstream end connected to the first end of the inline portion and a downstream end connected to the tubing connection, and a recycle circuit comprising a compressor having a compressor inlet that is in selective communication with the supply circuit and a compressor discharge that is in communication with the second end of the inline portion.

2. The system of claim 1, wherein the recycle circuit further comprises recycle tubing having an inlet end connected to the compressor discharge and an exit end connected to the second end of the inline portion so that communication between the compressor discharge and portable bottle is through the recycle tubing.

3. The system of claim 1, where the compressor is mounted to an exterior of the bottle.

4. The system of claim 1, further comprising a filter in the supply circuit that contains an air blocking material and a controller for use in calibrating the gas sensor unit.

5. The system of claim 1, where the test cap comprises a chamber that receives the sensor inlet, and seals on the inner surface of the chamber that define a pressure barrier between the test gas in the supply circuit and ambient.

6. The system of claim 1, the T fitting comprising a first T fitting, the system further comprising a second T fitting that selectively provides communication between the portable bottle, the test cap, and the compressor.

7. The system of claim 6, the recycle circuit further comprising a recycle valve that is selectively opened and closed and that is between the compressor and the second T-fitting.

8. A method of gas sensor testing comprising:
 flowing test gas from a portable bottle into a T fitting attached to the portable bottle and through a supply circuit to expose the gas sensor to an amount of test gas;
 monitoring an output from the gas sensor in response to being exposed to the test gas;
 determining the need for calibrating the gas sensor based on the output from the gas sensor; and
 recapturing the amount of the test gas by drawing test gas in the supply circuit into a recycle circuit, and directing the recaptured test gas back into the portable bottle through the T fitting.

9. The method of claim 8, wherein the T-fitting comprises a first T-fitting, and wherein the test gas is drawn into the recycle circuit through a second T-fitting that connects between the supply circuit and the recycle circuit.

10. The method of claim 8, further comprising directing the amount of test gas that is recaptured back to the test gas source.

11. The method of claim 8, further comprising using a compressor to draw the test gas into the recycle circuit, and wherein test gas in the portable bottle flows through the supply circuit without a compressor.

12. The method of claim 8, further comprising filtering non-test gas substances that have mixed with the amount of test gas during the step of recapturing the amount of test gas.

13. The method of claim 8, wherein in the supply circuit is another T fitting that provides selective communication between the supply circuit and the recycle circuit.

14. The method of claim 13, where a block valve is in the recycle circuit that is selectively opened during the step of recapturing.

15. The method of claim 14, where the block valve is selectively closed when gas is flowing through the supply circuit to expose the gas sensor to an amount of test gas.

16. The method of claim 15, where the block valve comprises a first block valve, wherein a second block valve is in the supply circuit between the T fitting and an intersection between the supply circuit and the recycle circuit, wherein the second block valve is open when test gas is flowing through the supply circuit to the gas sensor, and wherein the second block valve is closed when test gas is flowing through the first block valve.

* * * * *

UNITED STATES PATENT AND TRADEMARK OFFICE
CERTIFICATE OF CORRECTION

| | |
|---|---|
| PATENT NO. | : 11,604,179 B2 |
| APPLICATION NO. | : 16/799589 |
| DATED | : March 14, 2023 |
| INVENTOR(S) | : Alsalman et al. |

It is certified that error appears in the above-identified patent and that said Letters Patent is hereby corrected as shown below:

In the Claims

Column 7, Claim 1, Line 1 should read:
-- the test gas in the portable bottle and an opposite end --

Column 7, Claim 1, Line 6 should read:
-- cavity defined within the housing that selectively --

Column 7, Claim 1, Line 7 should read:
-- receives a sensor inlet that is on the gas sensor, and --

Signed and Sealed this
Ninth Day of May, 2023

*Katherine Kelly Vidal*

Katherine Kelly Vidal
*Director of the United States Patent and Trademark Office*